United States Patent [19]

Fruchey

[11] Patent Number: 4,855,499
[45] Date of Patent: Aug. 8, 1989

[54] NOVEL PROCESS TO PREVENT FORMATION OF CHLORINATED BY-PRODUCTS IN APAP PRODUCTION

[75] Inventor: Olan S. Fruchey, Corpus Christi, Tex.

[73] Assignee: Hoechst Celanese Corporation, Somerville, N.J.

[21] Appl. No.: 118,117

[22] Filed: Nov. 6, 1987

[51] Int. Cl.⁴ .......................................... C07C 102/10
[52] U.S. Cl. .................................... 564/223; 564/265
[58] Field of Search .......................................... 564/223

[56] References Cited

U.S. PATENT DOCUMENTS 4,524,217 6/1985 Davenport et al. ................. 564/223
4,560,789 12/1985 Davenport et al. ............ 564/223 X
4,568,763 2/1986 Davenport et al. ............ 564/223 X

OTHER PUBLICATIONS

Donaruma et al., *Organic Reactions*, vol. II, Chapter 1, pp. 1–157 (1960).

*Primary Examiner*—Charles F. Warren
*Assistant Examiner*—Carolyn S. Greason
*Attorney, Agent, or Firm*—Herbert M. Hanegan; Donald R. Cassady

[57] ABSTRACT

A novel process for the prevention of the formation of chlorinated by-products during the Beckmann rearrangement of 4-hydroxyacetophenone oxime to APAP by the addition of an inorganic iodide such as potassium iodide to the Beckmann rearrangement reactor is disclosed.

9 Claims, No Drawings

NOVEL PROCESS TO PREVENT FORMATION OF CHLORINATED BY-PRODUCTS IN APAP PRODUCTION

This invention relates to a novel process for the prevention of chlorinated by-products in the production of N-acetyl-para-aminophenol (APAP) by the Beckmann rearrangement of 4-hydroxyacetophenone oxime using thionyl chloride in liquid sulfur dioxide as the catalyst.

BACKGROUND OF THE INVENTION

U.S. Pat. No. 4,524,217, the entire disclosure of which is herein incorporated by reference, discloses a novel process for the preparation of N-acyl-hydroxy aromatic amines in general and specifically N-acetyl-para-aminophenol (APAP) which are prepared by reacting a hydroxy aromatic ketone such as 4-hydroxyacetophenone with a hydroxy amine salt in a base to obtain the ketoxime of the ketone, e.g., 4-hydroxyacetophenone (4-HAP) oxime and then subjecting the oxime to a Beckmann rearrangement in the presence of a catalyst to form said N-acyl-hydroxy aromatic amines. Although various materials can be used as the Beckmann rearrangement catalyst, it is preferred to use thionyl chloride in liquid sulfur dioxide.

Although the process for the production of APAP as set forth in U.S. Pat. No. 4,524,217 is very effective, it has been found that a certain chlorinated by-product is formed during the Beckmann rearrangement of the 4-hydroxyacetophenone oxime when using said thionyl chloride in liquid sulfur dioxide as the Beckmann rearrangement catalyst. The chlorinated by-product which is formed during said Beckmann rearrangement is 3-chloro-4-hydroxyacetanilide (CAPAP). CAPAP is merely chlorinated APAP in the 3 position and although the exact mechanism for its formation has not yet been determined, it was discovered as a trace impurity in the crude APAP from the Beckmann reactor and also in the final product.

Although the 3-chloro-4-hydroxyacetanilide which is formed during the Beckmann rearrangement of 4-hydroxyacetophenone oxime when using thionyl chloride and sulfur dioxide is not known to have any detrimental effects, there is some indication that 3-chloro-4-hydroxyacetanilide affects the color of the APAP over a period of time. Nevertheless, experiments are inconclusive and are affected by the manner in which APAP is purified, either a single or double crystallization, etc. However, as can well be appreciated by those skilled in the art, APAP is an important commodity of commerce being one of the most widely used over-the-counter analgesics. It goes without saying that for human consumption, this product should be as pure as possible and chlorinated by-products are definitely not desirable.

SUMMARY OF THE INVENTION

It has now been found that the formation of chlorinated by-products during the Beckmann rearrangement of 4-hydroxyacetophenone oxime in the presence of sulfur dioxide and thionyl chloride can be almost entirely eliminated by incorporating a small amount of an inorganic iodide such as sodium iodide or potassium iodide. It is to be noted that insofar as the chemistry of the reaction is concerned, other inorganic iodides can be used but since potassium iodide is already approved as the iodide source in iodized table salt, it should pose no health risk in APAP and therefore is the preferred iodide salt.

The novel process of this invention is carried out simply by adding an alkali metal iodide such as potassium iodide to the 4-hydroxyacetophenone oxime prior to carrying out the Beckmann rearrangement in said thionyl chloride and sulfur dioxide. The amount of metal iodide utilized is extremely small and very acceptable results have been obtained when using 0.2 wt. % of potassium iodide relative to the oxime. It should be realized that no particular advantage is gained in going over the 0.2 grams per 100 grams of 4-hydroxyacetophenone oxime but, obviously, such can be done if desired. The amount of inorganic iodide which should be added is that amount sufficient to substantially prevent the formation of chlorinated by-products and said amount is usually in the range varying from 0.02 grams to 2.0 grams of potassium iodide per 100 grams of 4-hydroxyacetophenone oxime which is subjected to the Beckmann rearrangement.

It should be immediately understood that the manner in which iodide is added to the Beckmann rearrangement reactor is by no means critical and it can be added directly to the reactor or it can be contained in a recycle stream such as sulfur dioxide. In fact, as will be demonstrated in some of the examples, it is not necessary to add iodide for every single run since some of the iodide initially added is present in the recycle $SO_2$ stream, and experiments to date have indicated that when the $SO_2$ containing the potassium iodide was recycle to a reactor into which fresh 4-hydroxyacetophenone oxime, thionyl chloride and make-up $SO_2$ were added, a total of four cycles could be carried out without the reappearance of 3-chloro-4-hydroxyacetanilide (CAPAP). Thus, this suggests that, commercially, potassium iodide would only be added to the first batch of a recycle series and any potassium iodide make-up added if and when production of CAPAP reappeared.

For reasons which are not completely understood, it appears that the presence of potassium iodide in the Beckmann reactor not only eliminates CAPAP production but also decreases other unknowns typically present in the reactor product. While not wishing to be bound by any theory of operation, it appears that the action of potassium iodide on other unknowns is reasonable if one assumes that these other unknowns are APAP oxidation products. The iodide can act as a sink for any oxidizing potential in the reactor. Also, chlorine is a known oxidizing agent and by removing the chlorine, the potassium iodide prevents not only chlorination but oxidation from occurring. The Beckmann rearrangement of 4-hydroxyacetophenone oxime utilizing sulfur dioxide and thionyl chloride is disclosed in U.S. Pat. No. 4,524,217.

The reaction can be carried out at any convenient temperature ranging from about 0° to 35° C. for a period of time ranging from 15 minutes to about 4 hours. The pressure is not narrowly critical and may be, for example, in the range of 80 millimeters of mercury to 10 atmospheres absolute. The amount of thionyl chloride utilized in relation to the 4-hydroxyacetophenone oxime is also not narrowly critical. The weight ratio of oxime to thionyl chloride ranges from 5:1 up to 300:1. However, the solubility of APAP in the sulfur dioxide increases as the thionyl chloride level increases. This increased solubility obviously affects product recovery. Thus, the least amount of thionyl chloride should be used in order to maximize product recovery.

The following examples will illustrate the best mode contemplated for carrying out the novel process of this invention.

EXAMPLES 1-24

In all the examples which follow, the experimental procedure which was used is as follows:

(1) An appropriate 1 liter Zipperclave liner was charged with 100 grams of 4-HAP oxime and 0.2 grams KI (if a KI run). The liner was placed in a reactor and the reactor sealed.

(2) The reactor was cooled to $-50°$ C. with dry ice/acetone bath and 500 grams of sulfur dioxide charged via vacuum transfer.

(3) At $-50°$ C., 0.7 ml of thionyl chloride were added via a syringe.

(4) The contents of the reactor were warmed via a water bath to room temperature and the reaction exotherm was not allowed to exceed 30° C. Temperature control was achieved by venting $SO_2$.

(5) The contents of the reactor were allowed to stand at room temperature for 30 minutes; no stirring was employed during the entire course of the run.

(6) The reactor contents were then cooled to $-50°$ C. and the resulting slurry poured into the appropriate liner for flashing $SO_2$.

(7) The liner was placed back in the reactor and the contents warmed to 30° C.

(8) After standing for 30 minutes at room temperature, the $SO_2$ was flashed off.

(9) The solids were placed in the appropriate slurry neutralization vessel which contained 250 ml of demineralized water and 0.1 gram of sodium dithionite.

(10) The pH of the slurry was adjusted to 6 with a 20% caustic solution.

(11) The slurry was filtered and the solids washed with 100 ml of demineralized water.

(12) A sample of the solids was dried in a vacuum oven at 60° overnight and then submitted for high performance liquid chromatography analysis.

The following tables will illustrate the results obtained utilizing the above-described procedures.

In Table I, the column reactor liner refers to the Zipperclave liner utilized in steps (1) through (5). The flasher liner refers to the liner used in steps (7) and (8). In all cases, the slurry neutralization vessel, i.e., steps (9) through (11) was 316 stainless steel.

TABLE I

| Example | Reactor Liner* | FND Liner | KI Present | CAPAP (PPM) | Unknowns (PPM) |
|---|---|---|---|---|---|
| 1 | 316SS | 316SS | No | 700 | 114 |
| 2 | 316SS | 316SS | Yes | ND | 71 |
| 3 | 316SS | 316SS | No | 270 | 126 |
| 4 | 316SS | 316SS | Yes | ND | 45 |
| 5 | 316SS | 316SS | No | 900 | 122 |
| 6 | 316SS | 316SS | Yes | ND | 88 |
| 7 | Glass | 904L | No | 620 | 94 |
| 8 | Glass | 904L | Yes | ND | 39 |
| 9 | Glass | 904L | No | 930 | 94 |
| 10 | Glass | 904L | Yes | ND | 58 |
| 11 | Glass | 904L | No | 1300 | 129 |
| 12 | Glass | 904L | Yes | ND | 51 |
| 13 | 904L** | 904L | No | 490 | 116 |
| 14 | 904L | 904L | Yes | ND | 44 |
| 15 | 904L | 904L | No | 200 | 99 |
| 16 | 904L | 904L | Yes | ND | 69 |
| 17 | 904L | 904L | No | 170 | 144 |
| 18 | 904L | 904L | Yes | ND | 53 |
| 19 | Teflon | 904L | Yes | ND | 59 |
| 20 | Teflon | 904L | No | 180 | 98 |
| 21 | Teflon | 904L | Yes | ND | 21 |
| 22 | Teflon | 904L | No | 106 | 71 |
| 23 | Teflon | 904L | Yes | ND | 21 |
| 24 | Teflon | 904L | No | 235 | 93 |

*In the case of the glass reactor metallurgy a Co—glass coupon was placed in a teflon liner.
**904L is high grade stainless steel.

From the above table, it can be seen that 4 sets of 6 experiments each were carried out using 4 different reactor liners and 2 different flasher liners. The results show that, irrespective of the reactor liner or the flasher liner, potassium iodide reduced the levels of CAPAP to such an extent that they were not detectable. As can be seen, unknowns were also reduced utilizing potassium iodide.

The following examples, Examples 25-28, will illustrate the recycle potassium iodide effect.

In these examples, the procedure that was followed was the same as that set forth for the previous examples with the exception that no new potassium iodide was added but only the amount that was contained in the recycle $SO_2$ stream was used. Thus, in step (1) of the experimental procedure previously set forth, no KI was added (after the initial run) and in step (2), the sulfur dioxide was from a preceding run and contained residual KI. The flashing of $SO_2$ was not carried out for Examples 25-27 but the reactor slurry was filtered and the $SO_2$ recycled to step (2). For Example 28, the $SO_2$ was flashed. The recycle was carried out for 4 separate cycles with the following results shown in Table II.

TABLE II

| Example | Recycle Number | CAPAP (PPM) | Unknowns (PPM) |
|---|---|---|---|
| 25 | 1 | ND* | 14 |
| 26 | 2 | ND | 35 |
| 27 | 3 | ND | 116 |
| 28 | 4 | ND | 118 |

*ND = None detected

As can be seen, a total of 4 cycles were run and absolutely no CAPAP was detected. The above examples illustrate the fact that fresh potassium iodide need not be added at every single run but only upon the appearance of undesirable by-products.

What is claimed is:

1. In the process for the production of N-acetyl-para-aminophenol by the Beckmann rearrangement of 4-hydroxyacetophenone oxime using thionyl chloride in liquid sulfur dioxide as a catalyst the improvement which comprises adding a small but effective amount of an inorganic iodide to the Beckmann rearrangement reactor in order oo minimize the formation of chlorinated by-products.

2. The process of claim 1 wherein said inorganic iodide is an alkali metal iodide.

3. The process of claim 2 wherein the inorganic metal iodide is potassium iodide.

4. The process of claim 1 wherein the inorganic iodide is added in an amount ranging from 0.02 to 2.0 grams per 100 grams of said 4-hydroxyacetophenone oxime.

5. The process of claim 2 wherein the inorganic iodide is added in an amount ranging from 0.02 to 2.0 grams per 100 grams of said 4-hydroxyacetophenone oxime.

6. The process of claim 3 wherein the inorganic iodide is added in an amount ranging from 0.02 to 2.0 grams per 100 grams of said 4-hydroxyacetophenone oxime.

7. The process of claim 1 wherein the amount of inorganic iodide added is about 0.2 grams per 100 grams of said 4-hydroxyacetophenone oxime.

8. The process of claim 2 wherein the amount of inorganic iodide added is about 0.2 grams per 100 grams of said 2-hydroxyacetophenone oxime.

9. The process of claim 3 wherein the amount of inorganic iodide added is about 0.2 grams per 100 grams of said 2-hydroxyacetophenone oxime.

* * * * *